United States Patent
Jeong et al.

(10) Patent No.: US 9,981,993 B2
(45) Date of Patent: May 29, 2018

(54) MANUFACTURING METHOD OF CARBON-SILICON COMPOSITE

(71) Applicant: OCI COMPANY LTD., Seoul (KR)

(72) Inventors: Eun-Hye Jeong, Seongnam-si (KR); Yo-Seop Kim, Seongnam-si (KR); Sung-Ho Jung, Seongnam-si (KR); Jeong-Hyun Ha, Seongnam-si (KR)

(73) Assignee: OCI COMPANY LTD., Seoul (KR)

(*) Notice: Subject to any disclaimer, the term of this patent is extended or adjusted under 35 U.S.C. 154(b) by 398 days.

(21) Appl. No.: 14/793,742

(22) Filed: Jul. 8, 2015

(65) Prior Publication Data
US 2016/0020465 A1    Jan. 21, 2016

(30) Foreign Application Priority Data
Jul. 17, 2014    (KR) .................. 10-2014-0090641

(51) Int. Cl.
*H01M 4/60* (2006.01)
*H01M 10/052* (2010.01)
(Continued)

(52) U.S. Cl.
CPC .......... *C07F 7/0803* (2013.01); *H01M 4/0471* (2013.01); *H01M 4/133* (2013.01);
(Continued)

(58) Field of Classification Search
CPC .... H01M 4/60; H01M 10/052; H01M 4/0471; H01M 4/602; H01M 4/133; H01M 3/134;
(Continued)

(56) References Cited

U.S. PATENT DOCUMENTS

| 2004/0151837 A1* | 8/2004 | Morita | .............. C01B 31/02 |
| | | | 427/372.2 |
| 2006/0035149 A1* | 2/2006 | Nanba | .............. H01M 4/0471 |
| | | | 429/218.1 |

(Continued)

FOREIGN PATENT DOCUMENTS

| CN | 1800094 A | 7/2006 |
| CN | 101931076 A | 12/2010 |

(Continued)

OTHER PUBLICATIONS

Korean Office Action dated Sep. 30, 2015 in connection with the counterpart Korean Patent Application No. 10-2014-0090641.

(Continued)

*Primary Examiner* — Kenneth J Douyette
(74) *Attorney, Agent, or Firm* — Hauptman Ham, LLP (57) ABSTRACT

Disclosed herein are a manufacturing method of a carbon-silicon composite, including: (a) preparing a slurry solution including silicon (Si)-block copolymer core-shell particles; (b) mixing the slurry solution with a carbon raw material to manufacture a mixed solution; (c) performing a primary carbonization process on the mixed solution, followed by pulverization, to manufacture a primary carbon-silicon composite; and (d) performing a secondary carbonization process on the primary carbon-silicon composite, followed by pulverization, to manufacture a secondary carbon-silicon composite, the carbon-silicon composite, an anode for a secondary battery manufactured by applying the carbon-silicon composite, and a secondary battery including the anode for a secondary battery.

14 Claims, 3 Drawing Sheets

(51) Int. Cl.
*C07F 7/08* (2006.01)
*H01M 4/04* (2006.01)
*H01M 4/133* (2010.01)
*H01M 4/134* (2010.01)
*H01M 4/1393* (2010.01)
*H01M 4/1395* (2010.01)
*H01M 4/36* (2006.01)
*H01M 4/38* (2006.01)
*H01M 4/587* (2010.01)

(52) U.S. Cl.
CPC ......... *H01M 4/134* (2013.01); *H01M 4/1393* (2013.01); *H01M 4/1395* (2013.01); *H01M 4/366* (2013.01); *H01M 4/386* (2013.01); *H01M 4/587* (2013.01); *H01M 10/052* (2013.01)

(58) Field of Classification Search
CPC ........ C07F 7/08; C07F 7/0801; C07F 7/0803; C07F 4/60
See application file for complete search history.

(56) References Cited

U.S. PATENT DOCUMENTS

| | | | |
|---|---|---|---|
| 2011/0054074 A1 | 3/2011 | Jonschker et al. | |
| 2011/0165467 A1* | 7/2011 | Yew | H01M 4/134 429/231.8 |
| 2011/0200874 A1* | 8/2011 | Ono | H01M 4/134 429/213 |
| 2012/0244428 A1* | 9/2012 | Park | H01M 4/13 429/211 |

FOREIGN PATENT DOCUMENTS

| | | |
|---|---|---|
| CN | 101944596 A | 1/2011 |
| CN | 103238238 A | 8/2013 |
| JP | 2004-178922 A | 6/2004 |
| JP | 2006-196338 A | 7/2006 |
| JP | 2012-501951 A | 1/2012 |
| KR | 20100138607 A | 12/2010 |
| KR | 1020130019761 A | 2/2013 |
| KR | 1020130024285 A | 3/2013 |
| KR | 1020130071071 A | 6/2013 |

OTHER PUBLICATIONS

Korean Notice of Allowance dated Apr. 14, 2016 corresponding to Korean Application No. 10-2014-0090641.
Japanese Office Action dated Jul. 12, 2016 in connection with the counterpart Japanese Patent Application No. 2015-133300.
Chinese Office Action dated Jun. 2, 2017 in connection with the counterpart Chinese Patent Application No. 201510425473.0.

* cited by examiner

MANUFACTURING METHOD OF CARBON-SILICON COMPOSITE

CROSS REFERENCE TO RELATED APPLICATION

This application claims the benefit of Korean Patent Application No. 10-2014-0090641, filed on Jul. 17, 2014, entitled "MANUFACTURING METHOD OF CARBON-SILICON COMPOSITE", which is hereby incorporated by reference in its entirety into this application.

TECHNICAL FIELD

The present invention relates to a manufacturing method of a carbon-silicon composite.

BACKGROUND ART

An anode material of a lithium secondary battery capable of implementing high capacity and power is required to be used for a battery for an information technology (IT) equipment or a battery for an automobile. Accordingly, silicon has attracted attention as the anode material of the lithium secondary battery with high capacity. For example, it is known that pure silicon has a high theoretical capacity of 4200 mAh/g.

However, as compared with a carbon-based material, silicon has deteriorated cycle property, which is still an obstacle to practical use. The reason is because when inorganic particles such as silicon, as an anode active material, are directly used as a material for absorption and release of lithium, conductivity between active materials is deteriorated due to a change in volume during a charge and discharge process, or the anode active material is separated from an anode current collector. That is, the inorganic particles such as silicon included in the anode active material absorb lithium by a charge process to expand so as to be about 300% to 400% in volume. In addition, when the lithium is released by a discharge process, the inorganic particles are contracted, and when the charge and discharge cycles are repeated, electrical insulation may occur due to empty space generated between the inorganic particles and the anode active material to cause rapid deterioration in cycle life, and therefore, the inorganic particles have a serious problem in being used for a secondary battery.

Further, as a value obtained by dividing an amount of lithium releasing during a discharge process by an amount of lithium absorbing during an initial charge process becomes higher, an amount of a cathode consumed when an initial charge and discharge cycle proceeds becomes smaller, which is advantages in view of an initial efficiency. However, the existing silicon-based anode active material has a problem of low initial efficiency.

In addition, a secondary battery for an automobile requires high power capable of maintaining capacity even under harsh charge and discharge condition. However, there are many cases in which the existing graphite-based anode active materials and silicon-based anode active materials do not exhibit high power under harsh condition.

DISCLOSURE

Technical Problem

In order to significantly improve initial efficiency, cycle life, and power properties of a secondary battery, an aspect of the present invention is to provide a manufacturing method of a carbon-silicon composite, including: excellently dispersing nano-sized silicon (Si)-block copolymer core-shell carbonization particles, performing a primary carbonization process, followed by pulverization, and performing a secondary carbonization process, followed by pulverization.

However, technical problems to be achieved in the present invention are not limited to the above-mentioned problems, and other problems will be clearly understood to those skilled in the art from the following descriptions.

Technical Solution

In accordance with one aspect of the present invention, there is provided a manufacturing method of a carbon-silicon composite, including: (a) preparing a slurry solution including silicon (Si)-block copolymer core-shell particles; (b) mixing the slurry solution with a carbon raw material to manufacture a mixed solution; (c) performing a primary carbonization process on the mixed solution, followed by pulverization, to manufacture a primary carbon-silicon composite; and (d) performing a secondary carbonization process on the primary carbon-silicon composite, followed by pulverization, to manufacture a secondary carbon-silicon composite.

The secondary carbonization process in (d) may be performed at a temperature higher than that of the primary carbonization process.

The pulverization in (c) and (d) may be performed by a milling method.

When it is assumed that a particle diameter at 90% cumulative mass particle size distribution, of the silicon (Si)-block copolymer core-shell particles in the slurry solution in (a), is D90, and that a particle diameter at 50% cumulative mass particle size distribution, of the silicon (Si)-block copolymer core-shell particles in the slurry solution in (a), is D50, $1 \leq D90/D50 \leq 1.5$, and $2\ nm < D50 < 160\ nm$ may be satisfied.

The carbon raw material in (b) may include at least one selected from the group consisting of natural graphite, artificial graphite, soft carbon, hard carbon, pitch, calcined coke, graphene, carbon nanotube, and combinations thereof.

The pitch may include components insoluble in quinoline (QI) of 0 wt % to 20 wt %, and may have a softening point (SP) of 10° C. to 120° C.

The primary carbonization process in (c) may be performed under a pressure of 1 to 20 bar at 400° C. to 600° C. for 1 to 24 hours.

When it is assumed that a particle diameter at 90% cumulative mass particle size distribution, of the primary carbon-silicon composite after the pulverization in (c), is D90, and that a particle diameter at 50% cumulative mass particle size distribution, of the primary carbon-silicon composite after the pulverization in (c), is D50, $1 \leq D90/D50 \leq 2.5$, and $3\ \mu m < D50 < 10\ \mu m$ may be satisfied.

The secondary carbonization process in (d) may be performed under a pressure of 0.5 to 20 bar at 900° C. to 1400° C. for 0.5 to 24 hours.

When it is assumed that a particle diameter at 90% cumulative mass particle size distribution, of the secondary carbon-silicon composite after the pulverization in (d), is D90, and that a particle diameter at 50% cumulative mass particle size distribution, of the secondary carbon-silicon composite after the pulverization in (d), is D50, $1 \leq D90/D50 \leq 2$, and $3\ \mu m < D50 < 10\ \mu m$ may be satisfied.

In accordance with another aspect of the present invention, there is provided a carbon-silicon composite manufactured by the manufacturing method as described above.

A mass ratio of silicon (Si) to carbon (C) may be 1:99 to 10:90.

In accordance with another aspect of the present invention, there is provided an anode for a secondary battery manufactured by coating an anode slurry on an anode current collector, the anode slurry including: the carbon-silicon composite as described above; a conductive material; a binder; and a thickening agent.

In accordance with still another aspect of the present invention, there is provided a secondary battery including the anode for a secondary battery as described above.

Advantageous Effects

The carbon-silicon composite manufactured by performing the primary carbonization process, followed by pulverization, and performing the secondary carbonization process, followed by pulverization according to the present invention includes significantly uniformly dispersed, nano-sized silicon (Si)-block copolymer core-shell carbonization particles, such that when the carbon-silicon composite is used for an anode active material for a secondary battery, initial efficiency, cycle life, and power properties of the secondary battery may be significantly improved.

BEST MODE

Hereinafter, exemplary embodiments of the present invention will be described in detail. However, the following examples are only provided as one embodiment of the present invention, and the present invention is not limited to the following Examples.

Carbon-Silicon Composite and Manufacturing Method Thereof

The present invention provides a manufacturing method of a carbon-silicon composite, including: (a) preparing a slurry solution including silicon (Si)-block copolymer core-shell particles; (b) mixing the slurry solution with a carbon raw material to manufacture a mixed solution; (c) performing a primary carbonization process on the mixed solution, followed by pulverization, to manufacture a primary carbon-silicon composite; and (d) performing a secondary carbonization process on the primary carbon-silicon composite, followed by pulverization, to manufacture a secondary carbon-silicon composite.

The step (a) is a step of preparing a slurry solution including silicon (Si)-block copolymer core-shell particles.

The slurry solution includes the silicon (Si)-block copolymer core-shell particles and a dispersion medium, wherein the silicon (Si)-block copolymer core-shell particle has a structure in which a block copolymer shell consisting of blocks having high affinity with silicon and blocks having low affinity with silicon is coated on a surface of a silicon core, on the basis of the silicon core. Here, the block copolymer shell of the silicon (Si)-block copolymer core-shell particle forms a spherical micelle structure in which the blocks having high affinity with silicon are gathered toward the surface of the silicon core by van der Waals force, and the like, and the blocks having low affinity with silicon are gathered toward the outer side.

A weight ratio between the silicon core and the block copolymer shell is preferably 2:1 to 1000:1, and more preferably, 4:1 to 20:1, but the present invention is not limited thereto. Here, when a weight ratio between the silicon core and the block copolymer shell is less than 2:1, a content of the silicon core possible to practically alloy with lithium in an anode active material is decreased, such that capacity of the anode active material is reduced, and an efficiency of a lithium secondary battery is deteriorated. Meanwhile, when a weight ratio between the silicon core and the block copolymer shell is more than 1000:1, a content of the block copolymer shell is decreased to deteriorate dispersibility and stability in the slurry solution, such that the block copolymer shell of the core-shell carbonization particles in the anode active material may not properly perform a buffer function.

The blocks having high affinity with silicon are gathered toward the surface of the silicon core by van der Waals force, and the like. Here, the blocks having high affinity with silicon are preferably poly acrylic acid, poly acrylate, poly methacrylic acid, poly methyl methacrylate, poly acrylamide, carboxymethyl cellulose, poly vinyl acetate, or polymaleic acid, and more preferably, poly acrylic acid, but the present invention is not limited thereto.

The blocks having low affinity with silicon are gathered toward the outer side by van der Waals force, and the like. Here, the blocks having low affinity with silicon are preferably poly styrene, poly acrylonitrile, poly phenol, poly ethylene glycol, poly lauryl methacrylate or poly vinyl difluoride, and more preferably, poly acrylonitrile, but the present invention is not limited thereto. Here, the block having low affinity with silicon has a high carbonization yield during a carbonization process, as compared to the block having high affinity with silicon.

The block copolymer shell is the most preferably a polyacrylic acid-polystyrene block copolymer shell. Here, the polyacrylic acid preferably has a number average molecular weight (Mn) of 100 g/mol to 100,000 g/mol, and the polystyrene has a number average molecular weight (Mn) of 100 g/mol to 100,000 g/mol, but the present invention is not limited thereto.

The slurry solution preferably includes the silicon particles at a high content, and when it is assumed that a particle diameter at 90% cumulative mass particle size distribution, in particle distribution in the slurry solution of the silicon (Si)-block copolymer core-shell particles, is D90, and when it is assumed that a particle diameter at 50% cumulative mass particle size distribution thereof, is D50, $1 \leq D90/D50 \leq 1.5$, and $2\ nm < D50 < 160\ nm$ are preferred, and $1 \leq D90/D50 \leq 1.4$, and $2\ nm < D50 < 120\ nm$ are more preferred, but the present invention is not limited thereto. The block copolymer shell of the silicon (Si)-block copolymer core-shell particle forms a spherical micelle structure on the basis of the silicon core to have excellent dispersibility in the slurry solution as compared to silicon particles without separate block copolymer, such that agglomeration phenomenon of particles is reduced to provide uniform distribution in which size deviation between particles is small, while obtaining a small value of D50 in the slurry solution, and the silicon (Si)-block copolymer core-shell carbonization particles may be more uniformly and excellently dispersed in a carbonaceous matrix.

In order to implement the slurry solution satisfying the above-described dispersion conditions, that is, about 1≤D90/D50≤about 1.5 and about 2 nm<D50<about 160 nm, various methods for improving dispersion may be used. In particular, in order to implement the slurry solution satisfying the dispersion conditions as above by using silicon powder having a relatively large particle diameter, various methods may be performed or applied in a combination way.

Examples of the method for improving dispersion may include a method of controlling kinds of dispersion medium, a method of adding an additive for improving dispersion to the slurry solution, an ultrasonication method of treating the slurry solution with ultrasonic wave, and the like. In addition to the exemplified methods as the method for improving dispersibility, various methods known in the art may be applied, and may also be applied in a combination way.

The dispersion medium may include one selected from the group consisting of N-methyl-2-pyrrolidone (NMP), tetrahydrofuran (THF), water, ethanol, methanol, cyclohexanol, cyclohexanone, methyl ethyl ketone, acetone, ethylene glycol, octyn, diethyl carbonate, dimethyl sulfoxide (DMSO) and combinations thereof.

The dispersion medium may be used to help the slurry solution to be excellently dispersed.

In order to disperse the slurry solution, various dispersion methods such as ultrasonication, fine mill, ball mill, three-roll mill, stamp mill, eddy mill, and treatment with homomixer, planetary centrifugal mixer, homogenizer, or vibration shaker, are preferably performed, and ultrasonication is more preferred, but the dispersion method is not limited thereto.

Specifically, the ultrasonication may be performed by treating the entire slurry solution in a batch type at the same time with ultrasonic wave, or by continuously circulating the slurry solution so that a portion of the slurry solution is continuously treated with ultrasonic wave.

Apparatuses for performing the ultrasonication are generally provided with a tip, and ultrasonic energy generated from an end of the tip end disperses silicon particles, such that there is a limitation in area in which the generated ultrasonic energy is transmitted. Accordingly, when it is attempted to perform the ultrasonication on a large amount of slurry solution, the continuous circulation type of ultrasonication in which a portion of the slurry solution is continuously treated with ultrasonic wave by continuously circulating the slurry solution may be performed rather than using the batch type of ultrasonication to thereby increase efficiency. That is, a larger amount of slurry solution may be treated by the continuous circulation type of ultrasonication under the same power in the same period of time.

As a specific processing condition, the batch type of ultrasonication may be performed by supplying a power of 100 Watt to 500 Watt for 30 seconds to 1 hour to treat 1000 ml or less of the slurry solution.

As another specific processing condition, the continuous circulation type of ultrasonication may be performed by supplying a power of 500 Watt for 30 seconds to 1 hour to treat the slurry solution in an amount of about 3600 ml per an hour.

As still another specific processing condition, 10 kHz to 100 kHz of ultrasonic waves may be used, but the present invention is not limited thereto.

Since silicon particles agglomerate to form a lump in a slurry solution prepared by simply mixing silicon powder in a dispersion medium, the silicon particles configuring the slurry solution has an increased average diameter, and a slurry to be prepared has a state in which the silicon particles are not uniformly dispersed.

Meanwhile, the slurry solution may be excellently dispersed by selecting appropriate kinds of dispersion medium, or performing additional processes for improving dispersion such as ultrasonication, and the like, as described above, such that the slurry solution may implement distribution property of about 1≤D90/D50≤about 1.5, and about 2 nm<D50<about 160 nm by using the excellently dispersed silicon particles. That is, even though powder having an average diameter of about 2 nm to about 200 nm, specifically, about 60 nm to about 150 nm is used as the silicon powder, the slurry solution in a state in which the silicon particles are uniformly dispersed in the dispersion medium may be obtained.

The step (b) is a step of mixing the slurry solution with the carbon raw material to manufacture the mixed solution.

The dispersion medium of the slurry solution may dissolve the carbon raw material. Therefore, the mixed solution may be manufactured by dissolving the carbon raw material in the slurry solution.

The carbon raw material is dissolved in the silicon slurry solution, and then, is carbonized while capturing the silicon (Si)-block copolymer core-shell particles in the carbonization process to form the carbon-silicon composite including the silicon (Si)-block copolymer core-shell carbonization particles captured and dispersed in the carbonaceous matrix.

The carbon raw material is a starting material for forming the carbonaceous matrix, may be used without classification between conductive and non-conductive carbon raw materials. The carbon raw material may include at least one selected from the group consisting of natural graphite, artificial graphite, soft carbon, hard carbon, pitch, coke, graphene, carbon nanotube, and combinations thereof. Specifically, as the carbon raw material, commercially available products of coal tar pitch or petroleum pitch may be generally used. Here, as the carbon raw material, pitch including components insoluble in quinoline (QI) of 0 wt % to 20 wt %, and having a softening point (SP) of 10° C. to 120° C. is preferred, but the present invention is not limited thereto.

The carbon raw material is carbonized by the subsequent carbonization to be formed as a carbon matrix including crystalline carbon, amorphous carbon, or both of crystalline carbon and amorphous carbon.

The step (c) is a step of performing the primary carbonization process on the mixed solution, followed by pulverization, to manufacture a primary carbon-silicon composite.

In the present invention, 'the carbonization process' refers to a process of firing a carbon raw material at a high temperature to remove inorganic materials while leaving carbon.

The primary carbonization process is preferably performed at a temperature lower than that of the secondary carbonization process, more preferably, under a pressure of 1 to 20 bar at 400° C. to 600° C. for 1 to 24 hours, but the present invention is not limited thereto. When the primary carbonization process is performed at a temperature less than 400° C., impurities except for carbon in the carbon raw material may not be removed, and when the primary carbonization process is performed at a temperature more than 600° C., a large amount of impurities may be removed at a time, such that a treatment process is difficult to be performed.

Here, a carbonization yield in the primary carbonization process may be 40 wt % to 80 wt %. By increasing the carbonization yield in the primary carbonization process, occurrence of volatile matters may be reduced, and disposal thereof may be easily performed, which makes an environmentally friendly process.

The pulverization after the primary carbonization process may be performed by methods known in the art, preferably, any one method selected from the group consisting of grinding, mixing and milling, more preferably, a milling method, but the present invention is not limited thereto. Specifically, the milling method is preferably any one method selected from the group consisting of fine mill, ball mill, three-roll mill, stamp mill, eddy mill, and jet mill, more preferably, jet mill, but the present invention is not limited thereto.

As confirmed in Comparative Examples 2 and 3 of the present invention, initial efficiency of a secondary battery manufactured by pulverization with jet-mil is more excellent than that of a secondary battery manufactured by pulverization with ball-mill.

Here, when it is assumed that a particle diameter at 90% cumulative mass particle size distribution, of the primary carbon-silicon composite after the pulverization, is D90, and that a particle diameter at 50% cumulative mass particle size distribution, of the primary carbon-silicon composite after the pulverization, is D50, $1 \leq D90/D50 \leq 2.5$, and $3 \mu m < D50 < 10 \mu m$ may be satisfied.

By the pulverization after the primary carbonization process as described above, the carbon-silicon composite may be pulverized in a slightly flexible state to increase pulverization efficiency, and to form uniform particles, thereby more improving initial efficiency and power property of the secondary battery.

The step (d) is a step of performing the secondary carbonization process on the primary carbon-silicon composite, followed by pulverization, to manufacture the secondary carbon-silicon composite.

The secondary carbonization process is preferably performed at a temperature higher than that of the primary carbonization process, more preferably, under a pressure of 1 to 20 bar at 900° C. to 1400° C. for 1 to 24 hours, but the present invention is not limited thereto. When the secondary carbonization process is performed at a temperature less than 900° C., impurities or functional groups except for carbon in the carbon raw material may not be completely removed, and when the secondary carbonization process is performed at a temperature more than 1400° C., generation of silicon carbide and melting of silicon may occur.

Here, a carbonization yield in the secondary carbonization process is preferably 80 wt % or more, more preferably, 90% or more, but the present invention is not limited thereto. That is, a carbonization the secondary carbonization process is higher than that of the primary carbonization process.

A method for the pulverization after the secondary carbonization process is the same as described above in the pulverization method after the primary carbonization process.

That is, as confirmed in Comparative Examples 2 and 3 of the present invention, initial efficiency of a secondary battery manufactured by pulverization with jet-mil is more excellent than that of a secondary battery manufactured by pulverization with ball-mill.

Here, when it is assumed that a particle diameter at 90% cumulative mass particle size distribution, of a secondary carbon-silicon composite after the pulverization, is D90, and that a particle diameter at 50% cumulative mass particle size distribution, of the secondary carbon-silicon composite after the pulverization, is D50, $1 \leq D90/D50 \leq 2$, and $3 \mu m < D50 < 10 \mu m$ may be satisfied.

Through the pulverization after the primary carbonization process as described above, uniform particles may be formed to more improve initial efficiency and power property of the secondary battery.

That is, in a case in which the primary carbonization process, followed by pulverization, and the secondary carbonization process, followed by pulverization are performed as described in the manufacturing method of the carbon-silicon composite according to the present invention, particles of which particle size is uniform and surface is round may be obtained by removing excessively pulverized particles. Accordingly, particles with rough surfaces in an initial charge and discharge process or side-reactions occurring from the excessively pulverized particles may be reduced to increase initial efficiency. In addition, in a case in which the particles become spherical and curvature of the surface becomes reduced, absorption/release of lithium is rapidly generated, such that power property may be significantly improved.

In addition, the present invention provides a carbon-silicon composite manufactured by the manufacturing method as described above.

In the process for manufacturing the composite by using the silicon (Si)-block copolymer core-shell carbonization particles together with the carbonaceous matrix, the silicon (Si)-block copolymer core-shell carbonization particles may not agglomerate to form the carbon-silicon composite in which the silicon (Si)-block copolymer core-shell carbonization particles are uniformly excellently dispersed in the carbonaceous matrix without largely agglomerating the silicon-polymer carbonization matrix particles, according to the manufacturing method of the carbon-silicon composite. As described above, the silicon (Si)-block copolymer core-shell carbonization matrix particles may be uniformly dispersed throughout the carbonaceous matrix of the carbon-silicon composite. When the carbon-silicon composite is applied for an anode active material for a secondary battery, a volume expansion problem in a charge and discharge process may be alleviated to improve cycle life property of the lithium secondary battery while effectively exhibiting high capacity of silicon property. In addition, even under harsh condition, that is, a condition where a discharge rate is high, power property may be improved to exhibit high capacity.

The carbon-silicon composite having much more uniformly and excellently dispersed silicon (Si)-block copolymer core=shell carbonization particles may exhibit much more excellent capacity even though it includes the same content of silicon. For example, the carbon-silicon composite may exhibit a capacity over about 80% of a theoretical capacity of silicon.

Specifically, the carbon-silicon composite may be formed into the spherical or spherical-like particles, and may have a particle diameter of 0.5 μm to 50 μm. When the carbon-silicon composite having the above-described range of particle size is applied for an anode active material for a lithium secondary battery, charge capacity due to the high capacity of silicon property may be effectively exhibited, initial efficiency may be increased, and a volume expansion problem in a charge and discharge process may be alleviated to thereby improve cycle life and power property of the lithium secondary battery.

The carbon-silicon composite preferably has a mass ratio of silicon (Si) to carbon (C) of 1:99 to 10:90, but the present invention is not limited thereto. The carbon-silicon composite has an advantage of containing a high content of silicon within the above-described numerical scope, and also may include the excellently dispersed silicon particles while containing the high content of silicon, such that a volume expansion problem caused in a charge and discharge process at the time of using the silicon as the anode active material, may be alleviated.

Here, the carbon-silicon composite rarely includes oxides which are possible to deteriorate performance of the secondary battery, such that an oxygen (O) content of the carbon-silicon composite is significantly low. Specifically, the core layer may have an oxygen (O) content of 0 wt % to 1 wt %. In addition, the carbonaceous matrix rarely includes other impurities and by-product compounds, and mostly consists of carbon. Specifically, the carbonaceous matrix may have a carbon (C) content of 70 wt % to 100 wt %.

Anode for Secondary Battery

The present invention provides an anode for a secondary battery in which an anode slurry is coated on an anode current collector, the anode slurry including: the carbon-silicon composite as described above; a conductive material; a binder; and a thickening agent.

The anode for a secondary battery is formed by coating the anode slurry including the carbon-silicon composite; a conductive material; a binder; and a thickening agent on an anode current collector, followed by drying and rolling.

As the conductive material, at least one selected from the group consisting of a carbon-based material, a metal material, a metal oxide, and an electrically conductive polymer may be used. Specifically, carbon black, acetylene black, Ketjen black, furnace black, carbon fiber, fullerene, copper, nickel, aluminum, silver, cobalt oxide, titanium oxide, a polyphenylene derivative, polythiophene, polyacene, polyacetylene, polypyrrole, polyaniline, and the like, may be used.

As the binder, various kinds of binder polymers such as styrene-butadiene rubber (SBR), carboxymethyl cellulose (CMC), vinylidene fluoride-hexafluoropropylene copolymer (PVDF-co-HFP), polyvinylidenefluoride, polyacrylonitrile, polymethylmethacrylate, and the like, may be used. The thickening agent is to control viscosity, and may include carboxymethyl cellulose, hydroxymethyl cellulose, hydroxyethyl cellulose, hydroxypropyl cellulose, and the like.

As the anode current collector, stainless steel, nickel, copper, titanium, or alloys thereof, and the like, may be used. Among them, copper or copper alloy is the most preferred.

The carbon-silicon composite; the conductive material; the binder; and the thickening agent may have a weight ratio of 70~91:5~10:2~10:2~10.

Secondary Battery

The present invention provides a secondary battery including the anode for a secondary battery as described above.

The carbon-silicon composite in which the nano-sized silicon (Si)-block copolymer core-shell carbonization particles are significantly uniformly dispersed and included as an anode active material for a secondary battery is used in the secondary battery, such that the secondary battery may have more improved charge capacity and cycle life property.

The secondary battery includes the anode for a secondary battery; a cathode including a cathode active material; a separator; and an electrolyte.

As materials used as the cathode active material, compounds capable of absorbing and releasing lithium, such as $LiMn_2O_4$, $LiCoO_2$, $LiNIO_2$, $LiFeO_2$, and the like, may be used.

As the separator insulating the electrodes between the anode and the cathode, olefin-based porous films such as polyethylene, polypropylene, and the like, may be used.

In addition, the electrolyte may be obtained by mixing and dissolving at least one electrolyte including lithium salt selected from the group consisting of $LiPF_6$, LiBF4, $LiSbF_6$, $LiAsF_6$, $LiClO_4$, $LiCF_3SO_3$, $Li(CF_3SO_2)_2N$, $LiC_4F_9SO_3$, $LiSbF_6$, $LiAlO_4$, $LiAlCl_4$, $LiN(C_xF_{2x+1}SO_2)(C_yF_{2y+1}SO_2)$ (provided that each of x and y is a natural number), LiCl, and LiI in at least one aprotic solvent selected from the group consisting of propylene carbonate, ethylene carbonate, butylene carbonate, benzonitrile, acetonitrile, tetrahydrofuran, 2-methyl tetrahydrofuran, γ-butyrolactone, dioxolane, 4-methyldioxolane, N,N-dimethylformamide, dimethylacetamide, dimethylsulfoxide, dioxane, 1,2-dimethoxyethane, sulfolane, dichloroethane, chlorobenzene, nitrobenzene, dimethyl carbonate, methyl ethyl carbonate, diethyl carbonate, methyl propyl carbonate, methyl isopropyl carbonate, ethyl propyl carbonate, dipropyl carbonate, diisopropyl carbonate, dibutyl carbonate, diethylene glycol, and dimethyl ether.

A plurality of secondary batteries may be electrically connected to each other to provide a middle- or large-sized battery module or a battery pack including the plurality of secondary batteries, wherein the middle- or large-sized battery module or the battery pack may be used as a power supply for at least any one middle- or large-sized device selected from power tools; electric vehicles including EV, hybrid electric vehicle (HEV), and plug-in hybrid electric vehicle (PHEV); electric trucks; electric commercial vehicles; or systems for energy storage.

Hereinafter, preferred embodiments of the present invention will be described to assist in understanding the present invention. However, the following exemplary embodiments are provided only to more easily understand the present invention. The present invention is not limited thereto.

EXAMPLE

Example 1

Manufacture of Anode Active Material for Secondary Battery

A polyacrylic acid-poly acrylonitrile block copolymer was synthesized from polyacrylic acid and poly acrylonitrile, by a reversible addition-fragmentation chain transfer method. Here, the polyacrylic acid had a number average molecular weight ($M_n$) of 4090 g/mol, and the poly acrylonitrile had a number average molecular weight ($M_n$) of 29370 g/mol. 0.25 g of the polyacrylic acid-poly acrylonitrile block copolymer was mixed with 44.75 g of N-methyl-2-pyrrolidone (NMP). 5 g of silicon (Si) particles each having an average particle diameter of 50 nm were added to 45 g of the mixed solution. The solution with the silicon (Si) particles added thereto was treated with 20 kHz ultrasonic wave for 30 minutes by ultrasonic horn, to prepare a slurry solution. Here, as results obtained by measuring distribution property of silicon (Si)-block copolymer core-shell particles, on the slurry solution by a dynamic light scattering method (measurement device: ELS-Z2 manufactured by Otsuka Electronics), D90/D50 was 1.37, and D50 was 92.8 nm.

120 g of pitch (QI: 4 wt %, SP: 30° C.) as a carbon raw material and 34 g of the slurry solution were mixed and dispersed, then distilled to remove NMP. Then, a primary carbonization was performed under a pressure of 7 bar at 500° C. for 6 hours, followed by primary pulverization by jet-mill, to manufacture a primary carbon-silicon composite having particle distribution of D90/D50=2.15, and D50=7.7 μm. Then, a secondary carbonization was performed under a pressure of 1 bar at 1000° C. for 1 hour, followed by secondary pulverization by jet-mill, to manufacture a secondary carbon-silicon composite having particle distribution of D90/D50=1.76, and D50=7 μm, thereby manufacturing a carbon-silicon composite. Here, in the final carbon-silicon composite, a mass ratio of silicon (Si) to carbon (C) was 4:96.

Manufacture of Anode for Secondary Battery

Carbon-Silicon Composite: Carbon black (CB), carboxymethyl cellulose (CMC), styrene-butadiene (SBR), and water were mixed at a weight ratio of 91:5:2:2 to prepare a composition for an anode slurry. The composition for an anode slurry was coated on a copper current collector, and dried and rolled in an oven at 110° C. for about 1 hour, to manufacture an anode for a secondary battery.

Manufacture of Secondary Battery

A coin cell-type secondary battery was manufactured by stacking the anode for a secondary battery, a separator, an electrolyte (a solvent obtained by mixing ethylene carbonate with dimethyl carbonate at a weight ratio of 1:1, and adding 1.0M $LiPF_6$ thereto), and a lithium electrode in sequence.

Example 2

A carbon-silicon composite was manufactured by the same condition as Example 1, except for performing a secondary carbonization process at 1100° C. for 1 hour, and an anode for a secondary battery and a secondary battery were also manufactured by applying the above-manufactured carbon-silicon composite.

Example 3

A carbon-silicon composite was manufactured by the same condition as Example 1, except for using pitch (QI: 0 wt %, SP: 110° C.) as a carbon raw material, and an anode for a secondary battery and a secondary battery were also manufactured by applying the above-manufactured carbon-silicon composite.

Comparative Example 1

A carbon-silicon composite was manufactured by the same condition as Example 1, except for performing the secondary carbonization process at 850° C. for 1 hour, and an anode for a secondary battery and a secondary battery were also manufactured by applying the above-manufactured carbon-silicon composite.

Comparative Example 2

A carbon-silicon composite was manufactured by the same condition as Comparative Example 1, except for omitting the primary pulverization process after the primary carbonization process, and performing the secondary carbonization process, followed by pulverization by ball-mill, and an anode for a secondary battery and a secondary battery were also manufactured by applying the above-manufactured carbon-silicon composite. Here, a secondary carbon-silicon composite exhibited a particle distribution of 50 μm or less and a pulverization yield of 60% or less.

Comparative Example 3

A carbon-silicon composite was manufactured by the same condition as Comparative Example 1, except for omitting the primary pulverization process after the primary carbonization process, and performing the secondary carbonization process, followed by pulverization by jet-mill, and an anode for a secondary battery and a secondary battery were also manufactured by applying the above-manufactured carbon-silicon composite. Here, a secondary carbon-silicon composite exhibited a particle distribution satisfying D50=7.9 μm and a pulverization yield of 30% or less.

Comparative Example 4

A carbon-silicon composite was manufactured by the same condition as Comparative Example 1, except for omitting the primary carbonization process, and an anode for a secondary battery and a secondary battery were also manufactured by applying the above-manufactured carbon-silicon composite.

Experimental Example 1

Charge and discharge properties of the secondary batteries manufactured by Examples 1 to 3 and Comparative Examples 1 to 4 were tested under the following conditions.

When it is assumed that 300 mA per 1 g is 1 C, charge conditions were controlled by a constant current at 0.2 C up to 0.01V and a constant voltage at 0.01V up to 0.01 C, and discharge conditions were followed by the constant current at 0.2 C up to 1.5V.

Table 1 below shows results of initial efficiency obtained by dividing an initial discharge capacity by an initial charge capacity, and results of discharge capacity retention rate (%) after 25 cycles obtained by converting a discharge capacity retention rate after 25 cycles based on the initial discharge capacity, into percent (%).

TABLE 1

|  | Initial Efficiency (%) | Discharge Capacity Retention rate (%) After 25 Cycles |
|---|---|---|
| Example 1 | 84.7 | 100 |
| Example 2 | 83.5 | 92 |
| Example 3 | 79.8 | 93 |
| Comparative Example 1 | 76.0 | 92 |
| Comparative Example 2 | 69.2 | 93 |
| Comparative Example 3 | 72.9 | 92 |
| Comparative Example 4 | 74.0 | 78 |

As shown in Table 1, it could be confirmed that the secondary batteries of Examples 1 to 3 manufactured by using the carbon-silicon composite manufactured by performing the primary carbonization process, followed by the primary pulverization by jet-mill and performing the secondary carbonization process at 1000° C. or more, as the anode active material, exhibited significantly improved initial efficiency; meanwhile, the secondary battery of Comparative Example 1 in which the secondary carbonization process was performed less than 1000° C. had low degree of carbon crystallization to increase unstability, and therefore, exhibited deteriorated initial efficiency.

In the secondary batteries of Comparative Examples 2 and 3, since the primary pulverization as well as the effect of temperature in the secondary carbonization process were omitted, the final carbon-silicon composites exhibited non-uniform particle distributions and had excessively pulverized particles present in a large amount, and therefore, the initial efficiency of each of Comparative Examples 2 and 3 was remarkably deteriorated as compared to that of Comparative Example 1.

Figure 1:
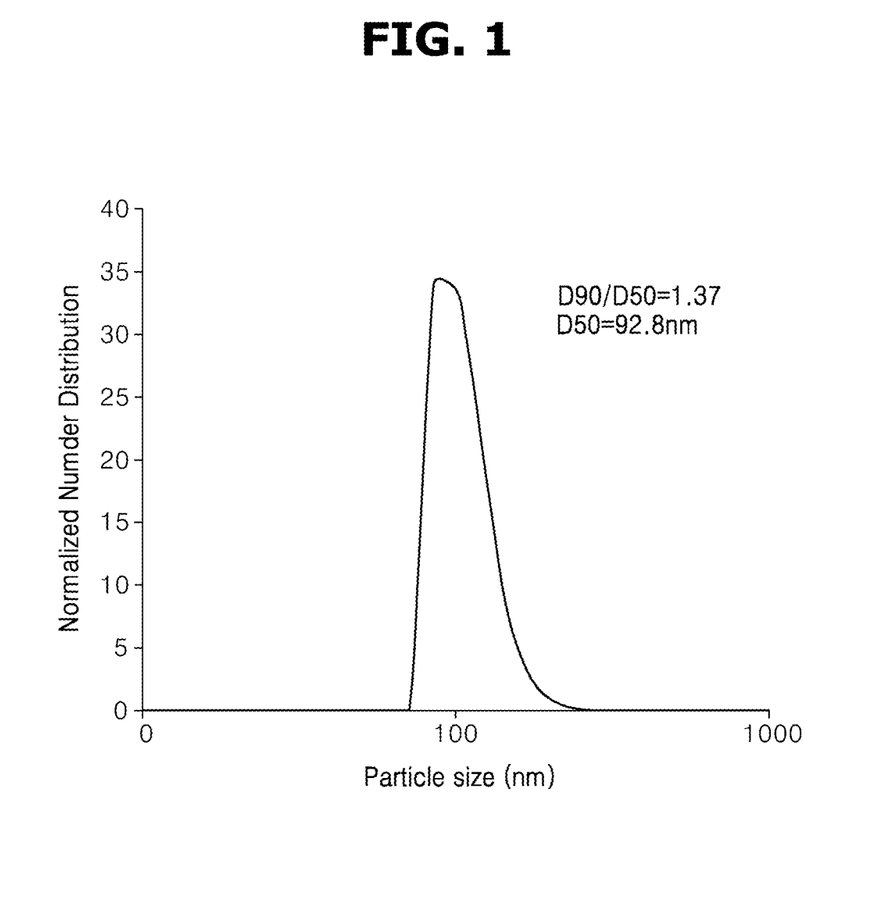
FIG. 1 is a graph showing distribution of silicon (Si)-block copolymer core-shell particles measured by a dynamic light scattering method on a slurry solution prepared by Example 1.
Figure 2:
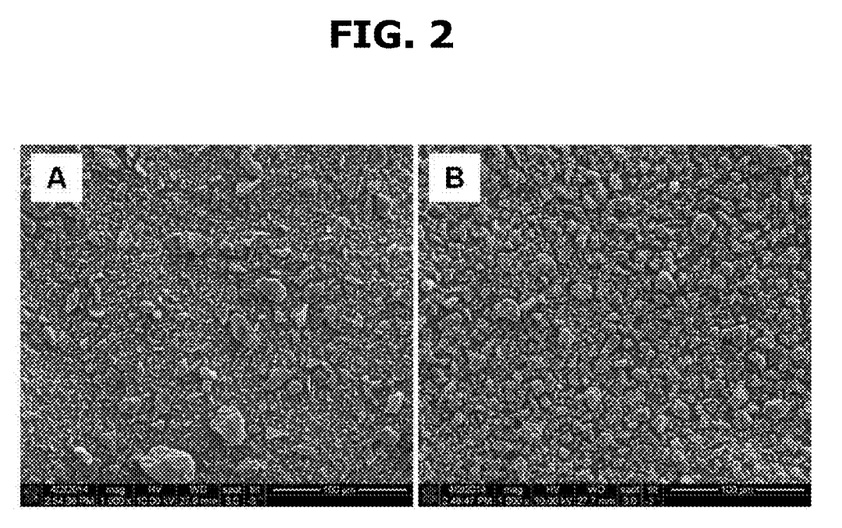
FIG. 2 is scanning electron microscope (SEM) images of final carbon-silicon composites manufactured by Comparative Example 3 (A) and Example 1 (B).

FIG. 2 is scanning electron microscope (SEM) images of final carbon-silicon composites manufactured by Comparative Example 3 (A) and Example 1 (B). As shown in FIG. 2, it could be confirmed in the final carbon-silicon composite of Comparative Example 3 (A) that particle distribution was not uniform and excessively pulverized particles (or smaller sized particles) were largely present, as compared to the final carbon-silicon composite of Comparative Example 1 (B).

In addition, it could be confirmed that the secondary batteries of Comparative Examples 1 to 3 manufactured by performing all of the primary carbonization process and the secondary carbonization process exhibited remarkable improvement in a problem of deterioration in discharge capacity after 25 cycles; meanwhile, the secondary battery of Comparative Example 4 manufactured by omitting the primary carbonization process and performing the secondary carbonization process only exhibited large deterioration in discharge capacity after 25 cycles, such that deterioration in capacity caused when silicon is typically used, was shown.

Meanwhile, pitch as the carbon raw material showed difference in charge and discharge results according to a content of components insoluble in quinoline (QI) and a softening point (SP). When the components insoluble in quinoline (QI) have a content of 0 wt % to 4 wt %, and the softening point (SP) is 30° C. to 110° C., the secondary battery exhibited improved initial efficiency and cycle life property.

In particular, it could be confirmed that the secondary battery of Example 1 used the carbon-silicon composite which was manufactured by using pitch having the components insoluble in quinoline (QI) of 4 wt %, and the softening point (SP) of 20° C. and performing the primary carbonization process, followed by the primary pulverization and performing the secondary carbonization process at 1000° C. or more, followed by the secondary pulverization, as the anode active material, to thereby exhibit significantly improved initial efficiency and cycle life property.

Experimental Example 2

Properties per discharge rate of the secondary batteries manufactured by Examples 1 and 2 and Comparative Example 1 were evaluated under the following conditions. When it is assumed that 300 mA per 1 g is 1 C, charge conditions were controlled by a constant current at 0.2 C up to 0.01V and a constant voltage at 0.01V up to 0.01 C, and discharge conditions were followed by the constant current at 0.2 C, 0.5 C, 1 C, and 2 C up to 1.5V every 5 cycles.

Figure 3:
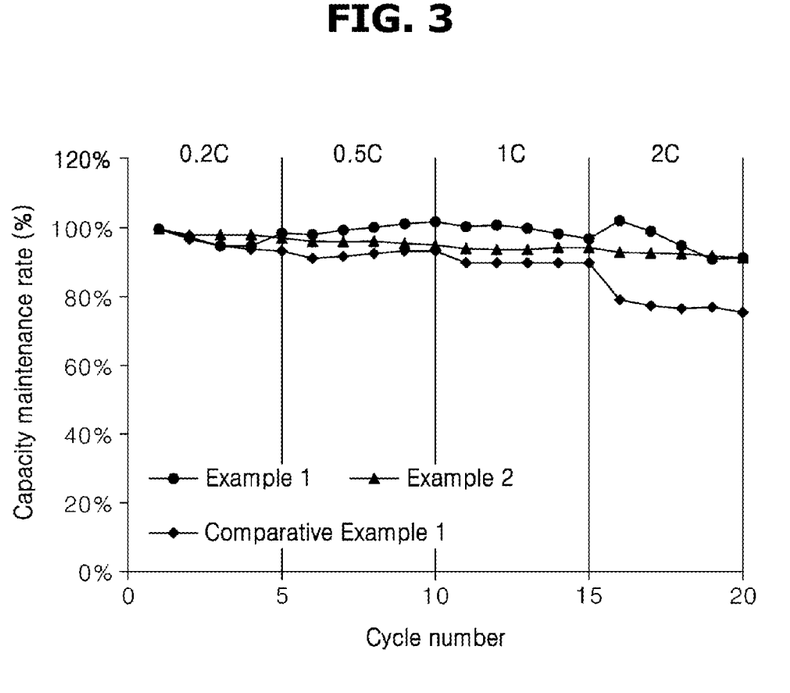
FIG. 3 is a graph showing capacity retention rate results according to each discharge rate, obtained by measuring capacities per discharge rate on the secondary batteries manufactured by Examples 1 and 2, and Comparative Example 1.

FIG. 3 is a graph showing capacity retention rate results according to each discharge rate, obtained by measuring capacities per discharge rate on the secondary batteries manufactured by Examples 1 and 2, and Comparative Example 1.

As shown in FIG. 3, the secondary batteries manufactured by Examples 1 and 2 had a high capacity retention rate even in a discharge process under increasingly harsh condition where the discharge rate was from 0.2 C to 2 C; meanwhile, the secondary battery manufactured by Comparative Example 1 exhibited deterioration in capacity retention rate from 0.2 C and rapid deterioration in capacity retention rate at 2 C.

That is, it could be confirmed that at the time of performing the secondary carbonization process at a high temperature of 1000° C. or more, the secondary battery had more improved power property.

The above description of the present invention is provided for illustrative purposes, and it will be understood to those skilled in the art that the exemplary embodiments can be easily modified into various forms without changing the technical spirit or essential features of the present invention. Accordingly, the exemplary embodiments described herein are provided by way of example only in all aspects and should not be construed as being limited thereto.

The invention claimed is:
1. A manufacturing method of a carbon-silicon composite, comprising:
  (a) preparing a slurry solution including silicon (Si)-block copolymer core-shell particles;
  (b) mixing the slurry solution with a carbon raw material to manufacture a mixed solution;
  (c) performing a primary carbonization process on the mixed solution to form silicon (Si) block copolymer core-shell carbonization particles captured and dispersed in carbonaceous matrix, followed by pulverization, to manufacture a primary carbon-silicon composite; and
  (d) performing a secondary carbonization process on the primary carbon-silicon composite, followed by pulverization, to manufacture a secondary carbon-silicon composite,
  wherein the carbon raw material is selected from coal tar pitch, petroleum pitch, or combinations thereof.
2. The manufacturing method of claim 1, wherein the secondary carbonization process in (d) is performed at a temperature higher than that of the primary carbonization process.
3. The manufacturing method of claim 1, wherein the pulverization in (c) and (d) is performed by a milling.
4. The manufacturing method of claim 1, wherein the silicon (Si)-block copolymer core-shell particles in the slurry solution satisfies dispersion conditions of $1 \leq D90/D50 \leq 1.5$, and $2 \text{ nm} < D50 < 160 \text{ nm}$.
5. The manufacturing method of claim 1, wherein the carbon raw material in (b) further comprises at least one selected from the group consisting of natural graphite, artificial graphite, soft carbon, hard carbon, pitch, calcined coke, graphene, carbon nanotube, and combinations thereof.
6. The manufacturing method of claim 5, wherein the pitch includes components insoluble in quinoline (QI) of 0 wt % to 20 wt %, and has a softening point (SP) of 10° C. to 120° C.
7. The manufacturing method of claim 1, wherein the primary carbonization process in (c) is performed under a pressure of 1 to 20 bar at 400° C. to 600° C. for 1 to 24 hours.
8. The manufacturing method of claim 1, wherein the primary carbon-silicon composite after the pulverization in (c) satisfies dispersion conditions of $1 \leq D90/D50 \leq 2.5$, and $3 \text{ μm} < D50 < 10 \text{ μm}$.

9. The manufacturing method of claim 1, wherein the secondary carbonization process in (d) is performed under a pressure of 0.5 to 20 bar at 900° C. to 1400° C. for 0.5 to 24 hours.

10. The manufacturing method of claim 1, wherein the secondary carbon-silicon composite after the pulverization in (d) satisfies dispersion conditions of 1≤D90/D50≤2, and 3 μm<D50<10 μm.

11. A carbon-silicon composite manufactured by the manufacturing method of claim 1.

12. The carbon-silicon composite of claim 11, wherein a mass ratio of silicon (Si) to carbon (C) is 1:99 to 10:90.

13. An anode for a secondary battery manufactured by coating an anode slurry on an anode current collector, the anode slurry including: the carbon-silicon composite of claim 12; a conductive material; a binder; and a thickening agent.

14. A secondary battery comprising the anode for a secondary battery of claim 13.

* * * * *